(12) United States Patent
Yue et al.

(10) Patent No.: US 6,887,895 B2
(45) Date of Patent: May 3, 2005

(54) PSEUDOLARIC ACID-B DERIVATIVES, THEIR PREPARATION AND PHARMACEUTICAL COMPOSITIONS

(75) Inventors: Jianmin Yue, Shanghai (CN); Shengping Yang, Shanghai (CN); Jian Ding, Shanghai (CN); Dong Xiao, Shanghai (CN); Shengtao Yuan, Shanghai (CN)

(73) Assignee: Shanghai Institute of Materia Medica Chinese Academy of Science, Shanghai (CN)

( * ) Notice: Subject to any disclaimer, the term of this patent is extended or adjusted under 35 U.S.C. 154(b) by 0 days.

(21) Appl. No.: 10/486,880

(22) PCT Filed: Aug. 14, 2002

(86) PCT No.: PCT/CN02/00562

§ 371 (c)(1),
(2), (4) Date: Feb. 13, 2004

(87) PCT Pub. No.: WO03/018591

PCT Pub. Date: Mar. 6, 2003

(65) Prior Publication Data

US 2004/0235944 A1 Nov. 25, 2004

(30) Foreign Application Priority Data

Aug. 14, 2001 (CN) .......................................... 011264799

(51) Int. Cl.[7] .................... A61K 31/366; C07D 311/78; C07D 311/94
(52) U.S. Cl. ....................................... 514/455; 549/281
(58) Field of Search ......................... 514/455; 549/281

(56) References Cited

PUBLICATIONS

Pan et al., Planta medica (1990), vol. 56, No. 4, pp. 383–385.*

* cited by examiner

Primary Examiner—Taofiq Solola
(74) Attorney, Agent, or Firm—Lowe Hauptman & Berner, LLP

(57) ABSTRACT

The invention relates to pseudolaric acid-B derivatives of general formula (I), wherein (a) $R_1$ is cyano, heterocyclyl, COXR' or CON(R")$_2$, wherein X is O or NH, R' is H, cycloalkyl, alkyl, heterocyclic alkyl or arylalkyl, each R" is independently alkyl, cycloalkyl or heterocyclicalkyl; (b) $R_2$ is H, alkylacyl, arylalkylacyl, arylacyl or heterocyclylacyl; (c) $R_3$ is COXY, amino or halogen, wherein X is O or NH, Y is H, $NH_2$, hydroxy, alkyl, cycloalkyl, heterocyclicalkyl, hetroatom-substituted alkyl, tertiary amino-substituted ammonioalkyl, aryl, arylalkyl or polyhydroxyalkyl. The invention also relates to processes for preparing such derivatives and antitumor or antifungal pharmaceutical compositions containing the same.

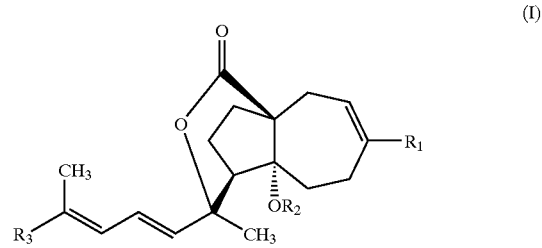

(I)

12 Claims, No Drawings

PSEUDOLARIC ACID-B DERIVATIVES, THEIR PREPARATION AND PHARMACEUTICAL COMPOSITIONS

TECHNICAL FIELD

The invention relates to semi-synthetic antitumor or antifungal medicines, especially relates to novel semi-synthetic pseudolaric acid derivatives, the processes for preparing such derivatives and antitumor or antifungal pharmaceutical compositions containing the same.

BACKGROUND OF THE INVENTION

It has been found in the recent investigations that pseudolaric acids and the compounds with correlative structures possess important biological activities. The methods for the isolation of such compounds and the pharmacologically experimental results have been disclosed in the following references:

1. Wu Saoxi, et al., *Chinese Journal of Dermatology*, 1960 (8): 18;
2. Li Zhulian, Zhou Bingnan, et al., "The proceeding of sino-American symposium on chemistry of Natural products", <<Chemistry of Natural Products>> (1982), pp.150–155;
3. Li Zhulian, Xu Guangyi, et al., "Study of new diterpenoids from *pseudolarix kaempferi*", *Acta Chimica Sinica*, 1982 (40): 447–456;
4. Wang Weichen, et al., "Action of anti-procreation of pseudolaric acid-B", *Acta Pharmacol. Sinica*, 1982 (3): 188–192;
5. Erguang Li, Alice M. Clark and Charles D. Hufford, "Antifugal evaluation of Pseudolaric acid B, a major constituent of *pseudolarix kaempferi*", *Journal of Natural Product*, 1995 (58): 57–67;
6. De-Ji Pan, Zhu-lian Li, et al., "The cytotoxic principles of *pseudolarix kaempferi*: Pseudolaric acid-A and -B and related derivatives", *Plant Medica*, 1990 (56): 383–385.

All the literatures mentioned above are incorporated herewith for reference.

It was reported that the angiogenesis in the tumor tissues was related with the malignant proliferation and metastasis of the tumor. The inhibition of tumor angiogenesis will lead to the decrease of supplies of oxygen and nutrition which were necessary for the tumor growth, then the tumor proliferation will be inhibited. Meantime, anti-angiogenesis also prevents the tumor metastasis because it can block the pathway through which tumor cells can enter into the blood circulation from tumor tissue via neonate capillaries.

The literatures in respect to the relationship between angiogenesis and cancers were listed as follows:

1. Cockerill G. W., Gamble T. R., Vadas M. A., "Angiogenesis: models and modulators", *Int. Rev. Cytol.*, Vol.159 (1995), pp.113–160;
2. Senger D. R., Van de water L., Brown L. F., et al., "Vascular permeability factor(VPF, VEGF) in tumor biology", *Cancer Metastasis Rev.*, Vol.12(1993), pp.303–324;
3. Donovan D., Harmey J. H., Redmond H. P. et al., "Ascites revisited: a novel role for tamoxifen", *Eur. J. Surg. Oncol.*, Vo.123(1997), pp. 570;
4. Ingber D, Fujita T., Kishimoto S. et al., "Synthetic analogues of fumagillin that inhabit angiogenesis and suppress tumor growth", *Nature*, Vol.348 (1990), pp. 555–560;
5. Jiang W. G., Puntis M. C. A., Hallett M. B., "molecular and cellular basis of cancer invasion and metastasis: implications for treatment", *Br. J. Surg.*, Vol.81 (1994), pp. 1576–1590;
6. Fidle I. J., Gerstein D. M., Hart I. R., "The biology of cancer invasion and metastasis", Adv. Cancer Res., Vol.28 (1978), pp.149–250;
7. Hanahan D., Folkman J., "Patterns and emerging mechanisms of the angiogenic switch during tumorigenesis", *Cell.*, Vol.86(1996), pp. 353–364;
8. Ferrara N., "The role of vascular endothelial growth factor in pathological angiogenesis", *Breast Cancer Res. Treat*, Vol.36(1995), pp. 127–137;
9. O'Reilly M., Holmgren L., Shing Y., et al., "Angiostain: anovel angenesis inhabitor that medicates the suppression of metastases by a Lewis lung carcinoma", *Cell.*, Vol.79 (1994), pp. 689–692;
10. O'Reilly M. S., Holmgren L., Chen C., et al., "Angiostatin induces and sustains domancy of human primary tumors in mice", *Nature Med.*, Vol.2 (1996), pp.689–692;
11. O'Reilly M. S., Boehm J., Shing Y., et al., "Endosatatin: an endogenous inhabitator of angiogenesis and tumor growth", *Cell.*, Vol.88 (1997), pp. 277–285;
12. Frank R. E., Saclarides T. J., Sue Leurgans, et al., "Tumor angiogenesis as a predictor of recurrence and survival in patients with node-negative colon cancer", *Ann. Surg.*, Vol.222 (1995), pp. 695–699.

All the literatures mentioned above are incorporated herewith for reference.

Although it was known that the use of angiogenesis inhibitors in the cancer chemotherapy could increase therapeutic effects and prevent the metastasis and relapse of the tumor, but no new drug targeting at angiogenesis has been marketed nowadays.

During long-time researches, the inventors have found that pseudolaric acids and new derivatives thereof could inhibit the growth of human microvascular endothelial cells, thus they could decrease supplies of oxygen and nutrition, which were necessary for tumor cells, by inhibiting the formation of blood vessels in the tumor tissue. Thereby, the cleavage and proliferation of tumor cells would be inhibited, resulting in the atrophy and vanishing of the tumor.

Accordingly, one purpose of the invention is to provide novel pseudolaric acid derivatives.

Another purpose of the invention is to provide a process for preparing said derivatives.

A further purpose of the invention is to provide antitumor or antifungal pharmaceutical compositions containing the same.

SUMMARY OF THE INVENTION

The invention provides pseudolaric acid derivatives having the following formula (I):

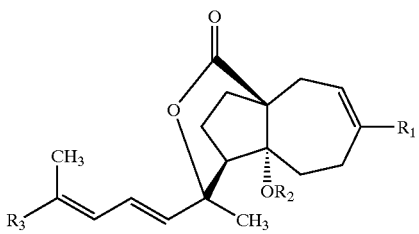

(I)

wherein (a) $R_1$ is a cyano, a heterocyclic group, $COXR'$ or $CON(R'')_2$, wherein X is O or NH, R' is H, a cycloalkyl, an alkyl, a heterocyclic alkyl or an arylalkyl, each R" is independently an alkyl, a cycloalkyl or a heterocyclic alkyl;

(b) $R_2$ is H, an alkylacyl, an arylalkylacyl, an arylacyl or a heterocyclic acyl; and (c) $R_3$ is COXY, an amino or a halogen, wherein X is O or NH, Y is H, $NH_2$, a hydroxy, an alkyl, a cycloalkyl, a heterocyclic alkyl, an alkyl substituted by oxygen(s), an aryl, an arylalkyl or a polyhydroxyalkyl, Provided that pseudolaric acid A, pseudolaric acid B, pseudolaric acid C, pseudolaric acid $C_2$, deacetoxyl pseudolaric acid A, deacetoxyl pseudolaric acid $C_2$, methyl pseudolarate A, deacetoxyl methyl pseudolarate A, p-bromine phenacyl pseudolarate A, methyl pseudolarate B, p-bromine phenacyl pseudolarate B, methyl pseudolarate C, propyl pseudolate C, iso-propyl pseudolate C, 19-demethoxyl iso-propyl pseudolarate B, 19-demethoxyl iso-propyl pseudolarate C, 19-propyoxyl pseudolarate B, 19-propoxyl pseudolaric acid C, 19-butoxyl pseudolaric acid B, and 19-butoxyl pseudolaric acid C are excluded.

The invention also provides the following processes for preparing pseudolaric acid derivatives having formula (I):

a. In case $R_1$ is CONHR or CONR'R", aminolyzing a compound of formula (I) wherein $R_1$ is COOR' in aqueous amine (said compound:said amine=1:1~1:300) in the presence of an acid catalyst at the conditions of temperature from −10° C. to 100° C. and pH 1–6;

b. In case $R_1$ is COOR', alcoholyzing a compound of formula (I) wherein $R_1$ is COOR' with an excess alcohol (said compound:said alcohol=1:1~1:500) in the presence of an alkaline catalyst under anhydrous condition at a temperature from 0° C. to the reflux temperature of the solvent and pH 9–14;

c. In case $R_2$ is alkylacyl, aryl-substituted alkylacyl, arylacyl or heterocyclylacyl, acylating a compound of formula (I) wherein $R_2$ is H (said compound:acylating agent= 1:5~1:500) at a temperature from 0° C. to 80° C.; or d. In case $R_3$ is COXY, reacting a compound of formula (I) wherein $R_3$=COOH with an excess acyl halogenating agent to form an acyl halide, then reacting said acyl halide with an alcohol or an amine in the presence of an acid scavenger at a temperature between −20~30° C.

The invention further provides a pharmaceutical composition for the treatment of tumors or inhibition of fungi, comprising a therapeutically effective amount of a pseudolaric acid-B derivative of formula (I) and a pharmaceutically acceptable carrier.

DETAILED DESCRIPTION OF THE INVENTION

Unless indicated otherwise, the substituents used herein have the following definitions: "alkyl" means a substituted or unsubstituted, saturated or unsaturated linear or branched alkyl chain, preferably, propyl, 2-methylpropyl or 2,2-dimethylpropyl; "cycloalkyl" means a substituted or unsubstituted 5- or 6-membered cycloalkyl, preferably, cyclohexyl; "aryl" means a substituted or unsubstituted, heterocyclic or nonheterocyclic aryl group; "arylalkyl" means an alkyl with substituted or unsubstituted aryl(s) thereon; "heterocyclic group" means a 5- or 6-membered heterocyclic group; "heteroalkyl" means a substituted or unsubstituted aromatic or non-aromatic heterocyclic alkyl, preferably, (α-furyl)methylene (furfural).

The preferred pseudolaric acid-B derivatives of the invention are those wherein $R_1$ is CONHR' or $CON(R'')_2$, $R_2$ is H, an alkylacyl, an arylalkylacyl, an arylacyl, or a heterocyclic acyl, and $R_3$ is —COOH.

The preferred pseudolaric acid-B derivatives of the invention are also those wherein $R_1$ is —COOR', $R_2$ is H, an alkylacyl, an arylalkylacyl, an arylacyl, or a heterocyclic acyl, and $R_3$ is —COOH.

The preferred pseudolaric acid-B derivatives of the invention are also those wherein $R_1$ is —COOR', $R_2$ is H, an alkylacyl, an arylalkylacyl, an arylacyl, or a heterocyclic acyl, and $R_3$ is COXY.

In the substituents of the compounds according to the invention, arranged by activities, preferred $R_1$ is an ester alkyl, preferred $R_2$ is an acetyl and preferred $R_3$ is a carboxyl or a (m-hydroxyanilino)acyl.

The compounds of the invention can be obtained via a several-step reaction by using pseudolaric acid-B or compounds having the stem nucleus of pseudolaric acid as a starting material, the preparation thereof was shown in De-Ji Pan, Zhu-lian Li, et al., "The cytotoxic principles of *pseudolarix kaempferi*: Pseudolaric acid-A and -B and related derivatives", *Plant medica*, 1990 (56): 383–385. The process for preparing the compounds of the invention is superior in mild reaction, simple method, high yield and easy industrialization.

The compounds of the invention can be prepared by adopting one of the following schemas or the combination of some of them.

(1)

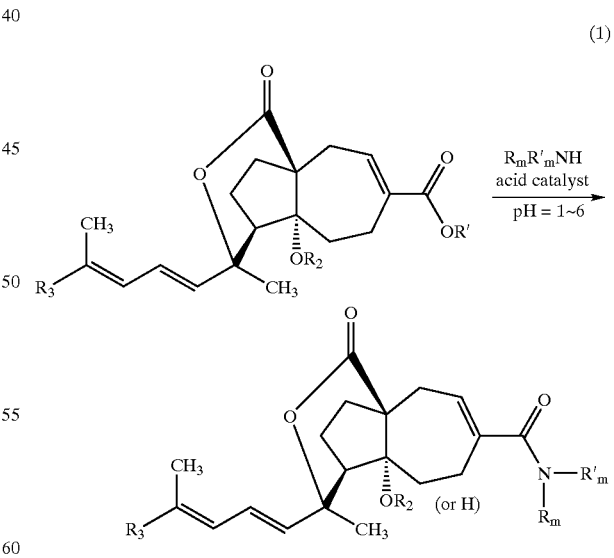

wherein, each of $R_m$ and $R'_m$, same or different, can independently be H, methyl, ethyl, propyl, pentyl or hexyl, or $R_m=R'_m=$—$(CH_2)_n$—, wherein n=2–5.

The acid catalyst can be selected from a group consisting of $H_2SO_4$, $H_3PO_4$, $CH_3CO_2H$ and HCl, preferrably, $CH_3CO_2H$.

The reaction can be conducted with stirring in water or an organic solvent. The organic solvent can be a liquid amine itself or benzene, chloroform, ether, tetrahydrofuran, etc. The temperature of the reaction is −10~100° C.

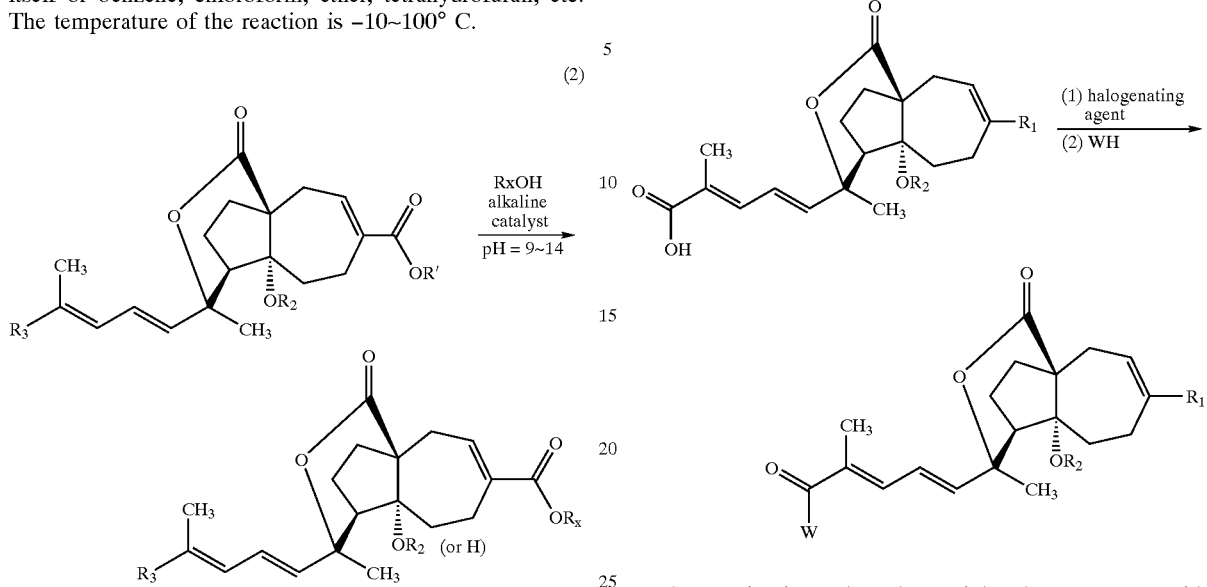

The alkaline catalyst can be selected from metal ammines, eg., sodium amide and potassium amide; and metal alkoxide, eg., sodium alkoxide and potassium alkoxide; preferably, sodium alkoxide and potassium alkoxide.

The reaction is conducted by stirring the reaction mixture in an anhydrous solvent, which itself is a reaction reagent or selected from other inert solvents, eg., anhydrous ether, tetrahydrofuran or tertiary butanol, etc. The temperature of reaction is from −4° C. to the reflux temperature of the solvent.

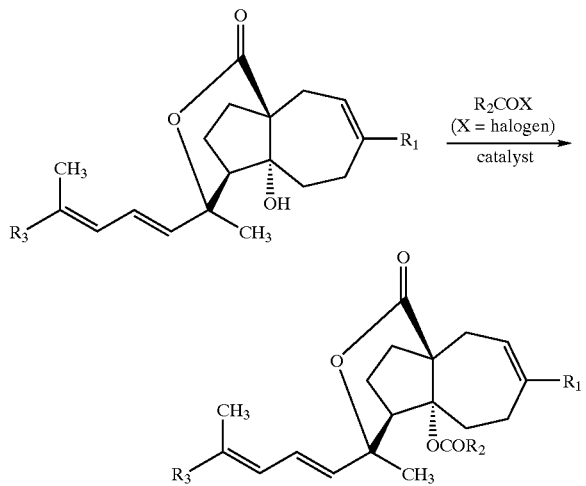

The catalyst in the above reaction can be DCC, AgCN, DMAP or pyridine, preferably, AgCN.

Generally, the acylating agent can be an acyl halide. When actyl chloride or propionyl chloride, etc., is used as an acylating agent, the catalyst can be omitted.

When the solvent is an acyl halide itself or aqueous ether, the reaction is conducted at peripheral temperatures with stirring or in reflux conditions.

The reaction is conducted at peripheral temperatures with stirring or in reflux conditions.

WH is an alcohol, a phenol, a primary amine or a secondary amine.

The acid scavenger can be an organic amine, $CaCO_3$, $K_2CO_3$, $Na_2CO_3$, $NaHCO_3$, KOH or NaOH, etc., preferably, $Na_2CO_3$ or $NaHCO_3$.

The composition according to the invention comprises a compound of the invention in an amount of safety and within a range of effective dosage and a pharmaceutically acceptable carrier.

"A safe and effective dosage" means that the amount of the compound is enough to obviously ameliorate conditions of diseases while not inducing serious side effects. The safe and effective dosage of the compound depends on specific conditions, such as the age of the patient, the condition of disease, the period of treatment, etc. Preferably, the composition of the invention includes the compound of the invention in an amount from 0.1% (by weight) to 99.9% (by weight), more preferably, from 20% (by weight) to 60% (by weight).

"The pharmaceutically acceptable carrier" means one or more compatible solid or liquid filler(s) or gel material(s) which are suitable to use for human and have enough purity and low enough toxicity. "Compatible" means, herein, that each of ingredients in the composition can be incorporated each other or with the compound of the invention, while no obvious decrease will be seen in the effect of the compound. Examples of the pharmaceutically acceptable carrier are as follows: sugars, eg., glucose, sucrose and lactose; starches, eg., corn starch and potato starch; cellulose and derivatives thereof, eg., carboxymethylcellulose sodium, ethylcellulose sodium and cellulose acetate, etc.; gelatin; talc; solid lubricants, eg., stearic acid and magnesium stearate, etc.; calcium sulfate; vegetable oils, eg., soya bean oil, sesame oil, peanut oil and olive oil, etc.; polyols, eg., propylene glycol, glycerin, mannitol and sorbitol, etc.; emulsifiers, eg., Tween®; lubricants, eg., sodium dodecyl sulfate; colouring agents; flavorings; stabilizers; antioxdants; preservatives; apyrogentity water; etc. The selection on the carrier depends on the administration manner of the compound. When the composition of the invention is used as an antitumor drug, it is preferably taken orally or parenterally, more preferably, parenterally. When the composition of the invention is used as an antifungal, it is preferably taken orally, topically or parenterally.

Preferred Embodiments

A part of the compounds prepared by using the process according to the invention have specific structures exemplified in Table 1.

TABLE 1

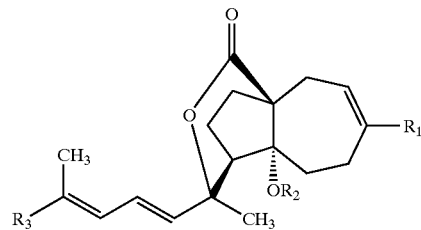

(I)

| No. | $R_1$ | $R_2$ | $R_3$ |
|---|---|---|---|
| PEX-1 | $CO_2CH_2CH(CH_3)_2$ | H | $CO_2H$ |
| PEX-4 | $CO_2CH_2CH_3$ | H | $CO_2H$ |
| PEX-4Y | $CO_2CH_2CH_3$ | AC | $CO_2H$ |
| PEX-6Y | $CO_2CH_3$ | AC | $CONH_2$ |
| PEX-7Y | $CO_2CH_3$ | AC | CONHOH |
| PEX-8Y | $CO_2CH_3$ | AC | $CON(CH_2)_2$ |
| PEX-9Y | $CO_2CH_3$ | AC | $CONHCH_2CH_2OH$ |
| PEX-10Y | $CO_2CH_3$ | AC | $CO_2CH_2CH_3$ |
| PEX-11Y | $CO_2CH_3$ | AC | $CONHC(CH_2OH)_3$ |
| EX-12Y | $CO_2CH_3$ | AC | $CONHCH_2CO_2H$ |
| PEX-13Y | $CO_2CH_3$ | AC | $CONHCH_2CONH_2$ |
| PEX-14Y | $CO_2CH_3$ | AC | COph |
| PEX-15Y | $CO_2CH_3$ | AC | CONH-(m-OH)ph |
| PEX-16Y | $CO_2CH(CH_3)_2$ | AC | $CO_2H$ |
| PEX-18Y | $CO_2CH_2ph$ | AC | $CO_2H$ |
| PEX-21 | $CO_2(CH_2)_2CH(CH_3)_2$ | H | $CO_2H$ |
| PEX-21Y | $CO_2(CH_2)_2CH(CH_3)_2$ | AC | $CO_2H$ |
| PEX-23Y | $CO_2CH_3$ | COph | $CO_2H$ |
| PEX-24Y | $CO_2CH_3$ | $COCH_2(P-Cl)ph$ | $CO_2H$ |
| PEX-25Y | $CO_2CH_2(\alpha\text{-furyl})$ | AC | $CO_2H$ |
| PEX-26Y | $CO_2CH_3$ | $CO(\alpha\text{-furyl})$ | $CO_2H$ |
| PEX-30Y | $CO_2CH_2(\alpha\text{-tetrafuryl})$ | AC | $CO_2H$ |
| PEX-30 | $CO_2CH_2(\alpha\text{-tetrafuryl})$ | H | $CO_2H$ |
| PEX-31Y | $CO_2CH_2(\text{cycloheptayl})$ | AC | $CO_2H$ |
| PAM-1Y | $CONH_2$ | AC | $CO_2H$ |
| PAM-2Y | $CONH_2$ | H | $CO_2H$ |
| PAM-5Y | $CONHCH_3$ | H | $CO_2H$ |
| PAM-7Y | $CON(CH_2CH_2)_2$ | H | $CO_2H$ |
| PAM-8Y | $CONHCH_3$ | AC | $CO_2H$ |
| PBX-1Y | $CO_2CH_2CH(CH_3)_2$ | AC | $CO_2H$ |
| PBX-2Y | $CO_2CH_2C(CH_3)_3$ | AC | $CO_2H$ |
| PBX-3Y | $CO_2Me$ | $CO(CH_2)_2CH_3$ | $CO_2H$ |
| PBX-4Y | $CO_2(CH)_2OH$ | AC | $CO_2H$ |
| PBX-5Y | 2-oxazoline | AC | $CO_2H$ |
| PBX-6Y | $CO_2CH_2CH(C_2H_5)_2$ | AC | $CO_2H$ |
| PBX-7Y | $CO_2CH_2CH(SCH_2)_2CH_2$ | AC | $CO_2H$ |
| PBX-8Y | $CO_2CH_2CH(CH_2CH_2)_2$ | AC | $CO_2H$ |
| PBX-9Y | $CO_2(CH_2)_2CH(CH_3)_2$ | AC | $CO_2H$ |
| PBX-10Y | $CO_2CH(CH_2)_2$ | AC | $CO_2H$ |
| PBX-11Y | $CO_2(CH_2)_3OCH_3$ | AC | $CO_2H$ |
| PBX-12Y | $CO_2(CH_2)_2OCH_3$ | AC | $CO_2H$ |
| PBX-13Y | $CO_2CH_2CH_2NH_2$ | AC | $CO_2H$ |
| PBX-14Y | $CO_2CH_2CH_2SCH_3$ | AC | $CO_2H$ |
| PBX-15Y | $CO_2CH_2CH_2CN$ | AC | $CO_2H$ |
| PBX-16Y | $CO_2CH_2CF_3$ | AC | $CO_2H$ |
| PBX-17Y | $CO_2CH_2CH(SCH_2)_2$ | AC | $CO_2H$ |

TABLE 2

MS and IR data of some compounds of the invention

| No. | ESI-MS Ionization type | Deprotonated ion peak | IR (cm$^{-1}$), KBr disc |
|---|---|---|---|
| PEX-1 | + | 455(M + 23) | — |
| PEX-4Y | + | 469(M + 23) | 3434.7, 1741.4, 1706.7, 1643.1 |
| PEX-4 | + | 427(M + 23) | — |
| PEX-6Y | + | 454(M + 23) | 3500, 3392.2, 1739.5, 1700, 1646.9 |
| PEX-7Y | + | 470(M + 1) | 3545, 3367.2, 1739.5, 1701, 1648.9 |
| PEX-8Y | + | 458(M + 1) | 3428.9, 1739.5, 1708.6, 1643.1 |
| PEX-9Y | + | 476(M + 1) | 3407.7, 1739.5, 1710.6, 1648.9 |
| PEX-10Y | + | 483(M + 23) | 3453.9, 1741.4, 1708.6, 1643.1 |
| PEX-11Y | + | 536(M + 1) | 3399.9, 1739.5, 1712.5, 1629.6 |
| PEX-12Y | − | 488(M − 1) | 3399.9, 1739.5, 1700, 1648.9 |
| PEX-13Y | − | 487(M − 1) | 3415.4, 1739.5, 1708.6, 1658.5 |
| PEX-14Y | + | 508(M + 1) | 3390.3, 1739.5, 1700.0, 1666.2, 1598.7, 1529.3, 1440.6, 756.0, 694.3 |
| PEX-15Y | − | 522(M − 1) | 3390.3, 1739.5, 1716.4, 1648.9, 1602.6, 1538.9, 1444.4, 775.3, 690.4 |
| PEX-16Y | + | 483(M + 23) | 3446.2, 1741.4, 1702.9, 1645.0 |
| PEX-18Y | + | 531(M + 23) | 1741.4, 1708.6, 1643.1 |
| PEX-21 | + | 469(M + 23) | — |
| PEX-21Y | + | 511(M + 23) | 3434.7, 1743.4, 1706.7, 1643.1 |
| PEX-23Y | + | 517(M + 23) | 3457.8, 1776.1, 1712.5, 1639.2 |
| PEX-24Y | + | 565(M + 23) | 3434.7, 1737.6, 1708.6, 1643.1 |
| PEX-25Y | + | 521(M + 23) | 3434.7, 1739.5, 1708.6, 1643.0, 1600.0, 1500.0 |
| PEX-26Y | − | 483(M − 1) | 3457.8, 1776.1, 1712.5, 1639.2, 1600, 1469.5 |
| PEX-30Y | + | 525(M + 23) | 3434.7, 1741.4, 1706.7, 1645.0 |
| PEX-31Y | − | 513(M − 1) | 3444.0, 1743.4, 1704.8, 1635.0 |
| PAM-1Y | — | — | 3430.8, 3203.2, 1743.4, 1689.4, 1635.0 |
| PAM-2Y | — | — | 3426.9, 1706.7, 1685.5 |
| PAM-5Y | — | — | 3390.3, 1712.5, 1654.7 |

TABLE 3

MS and $^1$HNMR data of some compounds of the invention
($^1$HNMR data of some compounds in Tab. 2 were omitted.)

| No. | ESI-MS Ionization type | Deprotonated ion peak | $^1$HNMR δ (ppm), J (Hz), Solvent is CD$_3$Cl unless otherwise mentioned |
|---|---|---|---|
| PEX-1 | — | — | 0.94(d, 6H, 16.6), 1.70(s, 3H), 1.95(d, 3H, 1.5), 3.88(dd, 2H, 1.8, 6.6), 5.93(d, 1H, 15.0), 6.55 (dd, 1H, 15.0, 11.4), 7.25(m, 2H). |
| PBX-1Y | — | — | 0.94(d, 6H, 6.6), 1.60(s, 3H), 1.98(s, 3H), 2.13 (s, 3H), 3.89(dd, 2H, 6.2, 1.8), 5.92(d, 1H, 15.0), 6.56(dd, 1H, J=15.0, 11.7), 7.20(m, 1H), 7.27(d, 1H, 11.7). |
| PBX-2Y | + | 497(M + 23) | — |
| PBX-3Y | — | — | 1.17(t, 3H, J=7.3), 1.60(s, 3H), 1.96(d, 3H, J=1.1), 2.41(q, 2H, J=8.1), 3.72(s, 3H), 5.92(d, 1H, J=15.0), 6.56(dd, 1H, J=15.0, 11.7), 7.22(m, 1H), 7.26(d, 1H, J=11.7). |
| PBX-4Y | — | — | 1.60(s, 3H), 1.96(s, 3H), 2.13(m, 3H), 3.86(t, 2H, 4.4), 4.27(m, 2H), 5.92(d, 1H, 15.0), 6.55 (dd, 1H, 15.0, 11.7), 7.26(m, 2H). |
| PBX-5Y | + | 488(M + 1) | — |
| PBX-6Y | + | 505(M + 23) | — |
| PBX-7Y | + | 551(M + 1) | — |
| PBX-8Y | − | 502(M − 1) | — |
| PBX-9Y | + | 511(M + 23) | — |
| PBX-10Y | + | 481(M + 23) | — |
| PBX-11Y | + | 513(M + 23) | — |
| PBX-12Y | + | 499(M + 23) | — |
| PBX-13Y | — | — | 1.45(s, 3H), 1.83(d, 3H, 1.1), 1.93(s, 3H), 3.21(t, 2H, 5.3), 3.53(t, 2H, 5.3), 5.81(d, 1H, 15.4), 6.39(dd, 1H, 15.4, 11.4), 7.09(d, 1H, 11.4) |
| PBX-14Y | + | 493(M + 1) | — |
| PBX-15Y | + | 472(M + 1) | — |
| PBX-16Y | − | 472(M − 1) | — |
| PBX-17Y | + | 559(M + 23) | — |

TABLE 3-continued

MS and $^1$HNMR data of some compounds of the invention
($^1$HNMR data of some compounds in Tab. 2 were omitted.)

| | ESI-MS | | |
|---|---|---|---|
| No. | Ionization type | Deprotonated ion peak | $^1$HNMR δ (ppm), J (Hz), Solvent is $CD_3Cl$ unless otherwise mentioned |
| PAM-7Y | — | — | (in $CD_3OD$: 1.42(s, 3H), 1.76(s, 3H), 3.32(m, 4H), 5.93(m, 2H), 6.37(dd, 1H, 14.9, 11.4), 7.06(d, 1H, 11.4) |
| PAM-8Y | — | — | 1.57(s, 3H), 1.94(s, 3H), 2.11(s, 3H), 2.81(d, 3H, 4.1), 5.89(d, 1H, 15.1), 6.4(m, 1H), 6.52 (dd, 1H, J=15.1, 11.6), 7.2(d, 1H, J=11.6). |

Compounds of the invention with preferred antitumor actions have the following structures:

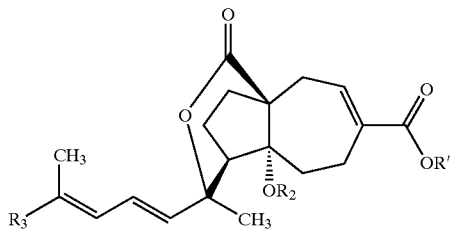

| No. | R | $R_3$ |
|---|---|---|
| PEX-15Y | methyl | (m-hydroxyanilino) acyl |
| PEX-25Y | (α-furyl) methylene | carboxyl |
| PEX-31Y | cyclohexylmethylene | carboxyl |

To evaluate the anti-tumor pharmacological activity of the compounds of the invention, the anti-proliferation activity thereof was assayed using P388 murin leukemia cells and A549 human lung adenocarcinoma cells; the anti-angiogenic activity, a newer target of antitumor, was measured using human microvascular endothelial cells (HMEC). Pseudolarix acid-B and hydroxycamptothecin were used as reference compounds in the evaluation.

P388, A549 and HMEC Proliferation Assay

Materials: DMEM was purchased from Gibco (Life Technologies, Grand Island, N.Y., USA). Sulforodamine B (SRB) and MTT were obtained from Sigma; TCA (acetic acid) and Tris base buffer were analytical pure products made in China.

SRB assay: Tumor (A549 and HMEC) cells in logarithmic growth were plated in DMEM media in the wells of a 96-well plate ($5 \times 10^3$ cells/90 μL/well) and serial dilutions of the compounds (10 μL) prepared in medium were added. Experiments at each concentration of compounds were performed in triplicate with controls of normal saline and cell-free withered wells. The plates were incubated at 37° C., 5% $CO_2$, for 72 hr. The media were decanted and cells were fixed with cold (4° C.) 10% trichloroacetic acid, followed by incubation at 4° C. for 1 hr. Then plates were washed with deionised water five times and allowed to air dry and stained by addition of 100 μL/well SRB solution [0.4% SRB (Sigma) in 1% acetic acid (W/V)] for 15 min. Following staining, plates were quickly washed five times with 1% acetic acid to remove unbound dye, and allowed to air dry. Bound dye was solubilized with Tris buffer (pH 10.5) prior to reading plates. The OD was measured with a multiwell spectrophotometer (VERSAmax, Molecular Devices, USA) at a wavelength of 520 nm.

MTT assay: P388 cells were seeded at a density of $1.5 \times 10^5$/ml into wells of 96-well plates and incubated with complete medium. After 24 hr, serial dilutions of the compounds (10 μL) prepared in medium were added. Experiments at each concentration of compounds were performed in triplicate with controls of cell-free withered wells and cell-free withered wells at corresponding concentration of compounds, if it is colored. The plates were incubated at 37° C., 5% $CO_2$, for 48 hr. Then, 20 μL aliquots of MTT (Sigma) solution (5 mg/mL) in saline were added directly to all the appropriate wells. The culture was continuously incubated for 4 hr. Then 50 μL "triplex solution" (10% SDS-5% isobutanol- 0.01M HCl) was added into each well. After the plates were incubated at 37° C. overnight, the values of absorbance at 520 nm were measured by using a plate reader (VERSA Max, Molecular Devices).

The rate of inhibition on the growth of cancer cells was calculated by the formula:

$$\text{Rate of growth inhibition} = [1 - (A_{520\ treated}/A_{520\ control})] \times 100\%$$

The result was also expressed as $IC_{50}$ (the drug concentration reducing by 50% the absorbance in treated cells, with respect to untreated cells) that was calculated by Logit method. The mean $IC_{50}$ was determined according to the data from three independent tests.

Preferred compounds of the invention screened by P388 model are as follows, the structures thereof were shown in Table 1.

| No. | $IC_{50}$ (mol/L) | No. | $IC_{50}$ (mol/L) |
|---|---|---|---|
| PEX-4Y | $4.4 \times 10^{-8}$ | PEX-17Y | $1.6 \times 10^{-10}$ |
| PEX-18Y | $4.8 \times 10^{-10}$ | PEX-21Y | $<1.0 \times 10^{-10}$ |
| PEX-20Y | $3.4 \times 10^{-10}$ | PEX-25Y | $<1.0 \times 10^{-10}$ |
| PEX-24Y | $2.6 \times 10^{-10}$ | PEX-31Y | $<1.0 \times 10^{-10}$ |
| PEX-30Y | $<1.0 \times 10^{-10}$ | Pseudolarix acid-B | $8.3 \times 10^{-10}$ |

Preferred compounds of the invention screened by A549 model are as follows, the structures thereof were shown in Table 1.

| No. | $IC_{50}$ (mol/L) | No. | $IC_{50}$ (mol/L) |
|---|---|---|---|
| PEX-14Y | $9.8 \times 10^{-8}$ | PEX-15Y | $15 \times 10^{-8}$ |
| PEX-18Y | $1.3 \times 10^{-8}$ | PEX-25Y | $5.5 \times 10^{-8}$ |
| PEX-24Y | $6.9 \times 10^{-8}$ | | |
| PEX-31Y | $<1.0 \times 10^{-10}$ | Pseudolarix acid-B | $2.8 \times 10^{-8}$ |

Preferred compounds of the invention screened by HMEC model, the structures thereof were shown in Table 1.

| No. | IC$_{50}$ (mol/L) | No. | IC$_{50}$ (mol/L) |
|---|---|---|---|
| PEX-8Y | 9.6 × 10$^{-7}$ | | |
| PEX-25Y | 1.0 × 10$^{-9}$ | | |
| Pseudolarix acid-B | 8.0 × 10$^{-8}$ | hydroxycamptothecin | 4.7 × 10$^{-7}$ |

The results of pharmacological screening has shown that the growth inhibition of many compounds of the invention on P388 and A549 cells was better than that of pseudolarix acid-B. In HEMC model, the activities of some compounds were better than or equivalent to hydroxycamptothecin. The activities of several compounds exceeded that of pseudolarix acid-B or hydroxycamptothecin in all of P388, A549 and HMEC models. Among them, some compounds are expectantly to become novel antitumor drugs.

Screening on Antifungal Activities

The action on *Candida albicans* was observed using liquid diluting method. The drug concentration in the tube in which no growth of fungus observed is the minimun inhibition concentration.

The action on *Trichophyton rubrum* was observed using agar diluting method. The drug concentration in the Petridish on which no growth of fungus observed is the minimun inhibition concentration. The specific determination was seen in the reference: Zhang Zuoran ed., <<Experiment of Medical Microorganism>>, Science Publishing House, 1998, pp.102–103.

Preferred antifungal compounds of formula (I) wherein R$_1$ is CO$_2$R', R$_2$ is acetyl, R$_3$ is carboxyl, are as follows. Pseudolarix acid-B is a reference compound.

| No. | R' | MIC (μg/ml) (*Candida albicans*) | MIC (μg/ml) (*Trichophyton rubrum*) |
|---|---|---|---|
| PEX-4Y | ethyl | 6.25 | 12.5 |
| PEX-25Y | (α-furyl)methylene | 6.25 | 12.5 |
| Pseudolarix acid-B | | 12.5 | 50.0 |

The results of the antifungal screen has shown that some of the compounds of the invention have superior activities in comparison with pseudolarix acid-B and they are expected to become novel antifungal drugs.

The invention will be further illustrated by the following examples, but these examples are by no means intended to limit the invention.

EXAMPLE 1

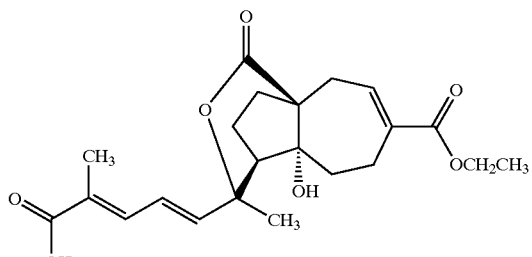

PEX-4

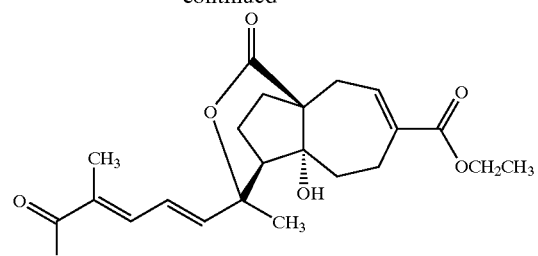

PEX-4Y

Step 1:

0.060 g (0.139 mmol) of pseudolaric acid B and 10 mL of anhydrous ethanol were added to a 25 mL round bottom flask. After the mixture was stirred at room temperature, it was adjusted with sodium ethylate (prepared by the reaction of metal sodium and anhydrous ethanol) to about pH 12. The reaction was then monitored by TLC till pseudolaric acid B disappeared. After the mixture was neutralized with acetic acid dropwise to pH=6, ethanol was removed on a rotatory evaporator. The residue was suspended in 10 mL water and then extracted with ethyl acetate three times. The organic phases were combined and ethyl acetate was removed on a rotatory evaporator, thus obtaining a crude product of compound PEX-4, which can be further purified by silica gel column chromatography to obtain a pure product.

$^1$HNMR (CDCl$_3$) δ(ppm): 1.25 (t, 3H, J=7.13Hz), 1.56 (S, 3H), 1.91 (S, 3H), 4.12 (m, 2H), 6.18 (d, 1H, J=15.11Hz), 6.52 (dd, 1H, J=15.11, 11.24Hz), 7.13(m, 1H), 7.22(d, 1H, J=11.24Hz).

Compounds PEX-1, PEX-19 to PEX21 and PEX-30 were prepared in similar methods.

Step 2:

10 mL of acetyl chloride was added to the reaction bottle with the above crude product. The reaction bottle was sealed and the mixture was stirred with an electromagnetic stirrer. The reaction was monitored by TLC per hour till compound PEX-4 disappeared. The reaction was completed after about 5 h, then exceeding acetyl chlorine was removed on a rotatory evaporator and 10 mL water was added. The water phase was extracted with ethyl acetate three times. The organic phases were combined and evaporated to dry under reduced pressure. The residue was loaded on a silica gel column (H60) and eluted with petroleum:ethyl acetate:formic acid=3:1:0.1 to afford 0.0535 g of compound PEX-4Y, as a white solid (yield 86.4%).

$^1$HNMR (CDCl$_3$) δ(ppm): 1.27(t, 3H, 7.23Hz), 1.59(S, 3H), 1.95(S, 3H), 2.11(S, 3H), 4.15(m, 2H), 5.91(d, 1H, J=15.02Hz), 6.54(dd, 1H, J=15.02, 11.42Hz), 7.18(m, 1H), 7.25(d, 1H, J=11.42Hz). IR(KBr) (cm$^{-1}$): 3434.7, 1741.4, 1706.7, 1643.1.

Compounds PEX-1Y to PEX-31Y and compounds PBX-1Y to PBX-17Y were prepared in similar methods.

EXAMPLE 2

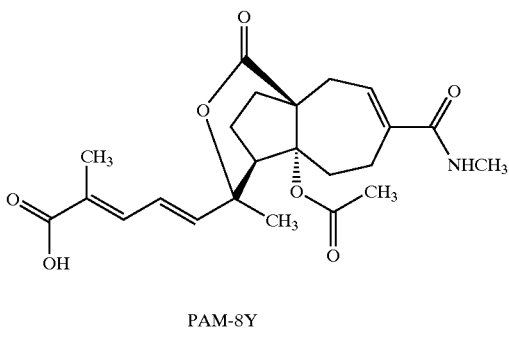

PAM-8Y 0.432 g (1 mmol) of pseudolaric acid B was suspended in 40 ml of distilled water and 1.5 mmol aqueous methylamine (28%) was added at room temperature. Then 0.5 mmol acetic acid was added. The reaction was kept at ordinary temperature and pressure with stirring. The monitor of TLC showed that the reaction completed after about 6 h. Then, the reaction mixture was diluted by 60 mL of water and extracted with ethyl acetate five times. The organic phase was dried on anhydrous sodium sulfate overnight, and then filtered. The filtrate was evaporated to remove ethyl acetate. The residue was subjected to a silica gel column and eluted with chloroform:methanol=15:1 to yield 0.400 g of PAM-8Y, as a light yellow solid (92.8%).

$^1$HNMR (CDCl$_3$) δ (ppm): 1.57(s, 3H), 1.94(s, 3H), 2.10(s, 3H), 2.81(d, 3H, J=4.11Hz), 5.89(d, 1H, J=15.08Hz), 5.91(brs, 1H), 6.42(m, 1H), 6.52(dd, 1H, J=15.08, 11.57Hz), 7.23(d, 1H, J=11.57Hz). IR (KBr) (cm$^{-1}$): 3390.3, 1712.5, 1654.7, 1612.2.

Compounds PAM-1Y to PAM-8Y were prepared in similar methods.

EXAMPLE 3

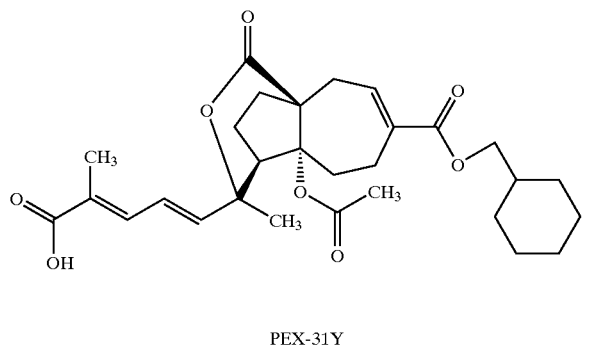

PEX-31Y 0.05 g (0.116 mmol) of pseudolaric acid B and 3 mL cyclohexyl methanol of were added into a flask. To this mixture, powdered potassium t-butoxide was added in batch with stirring at room temperature to adjust the mixture to pH 13. The flask was sealed and the mixture was stirred for 24 h. The monitor of TLC showed that the reaction completed, then the reaction mixture was neutralized with anhydrous acetic acid to pH=6. After the removal of cyclohexyl methanol and ethanol, the residue was subjected to silica gel comlumn chromatography (petroleum:ethyl acetate:formic acid=3:1:0.1) to afford 0.032 g of PEX-31Y, as a light yellow solid (55.0%).

$^1$HNMR (CDCl$_3$) δ (ppm): 1.55(s, 3H), 1.94(s, 3H), 2.10(s, 3H), 3.89(m, 2H), 5.89(d, 1H, J=15.01Hz), 6.52(dd, 1H, J=15.01, 11.35Hz), 7.19(m, 1H), 7.26(d, 1H, J=11.35Hz). IR (KBr) (cm$^{-1}$): 3444, 1743.4, 1704.8, 1635.0.

EXAMPLE 4

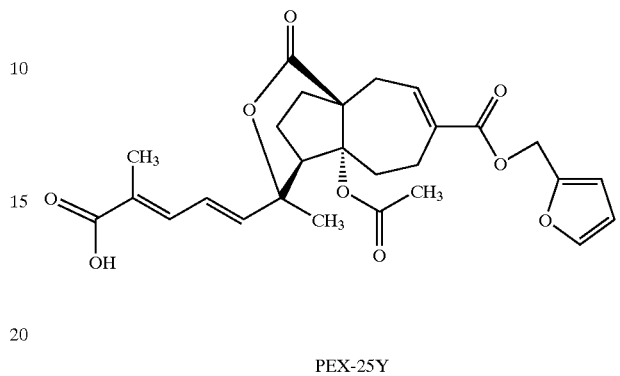

PEX-25Y 0.050 g (0.116 mmol) of pseudolaric acid B and 2 mL of dry α-furfuryl methanol were added into a 10 mL flask equipped with a reflux condenser and a calcium chloride tube, and the powder of potassium t-butoxide was added in batch with stirring at room temperature to adjust the mixture to pH 11. The mixture was stirred for 3 h at room temperature, then heated to 80–90° C. overnight. After being adjusted to pH 6 with acetic acid, the reaction solution was distilled under reduced pressure to remove furfuryl alcohol and ethanol. The residue was purified by silica gel column chromatography (petroleum:ethyl acetate:water=3:1:0.1) to obtain a brown solid, followed by RP-18 column chromatography (methanol:water=7:3) to afford 0.045 g of compound PEX-25Y, as a light yellow solid (yield 78.1%).

$^1$HNMR (CDCl$_3$) δ(ppm): 1.59 (s, 3H), 1.91(s, 3H), 2.13 (s, 3H), 5.04 (d, 1H, J=13.2Hz), 5.15 (d, 1H, J=13.2Hz), 5.91(d, 1H, J=14.8Hz), 6.38 (d, 1H), 6.55 (dd, 1H, J=14.8, 11.6Hz), 7.21–7.27 (m, 4H). IR (KBr) (cm$^{-1}$): 3434.7, 1739.5, 1708.6, 1643.1, 1600.0, 1500.0.

EXAMPLE 5

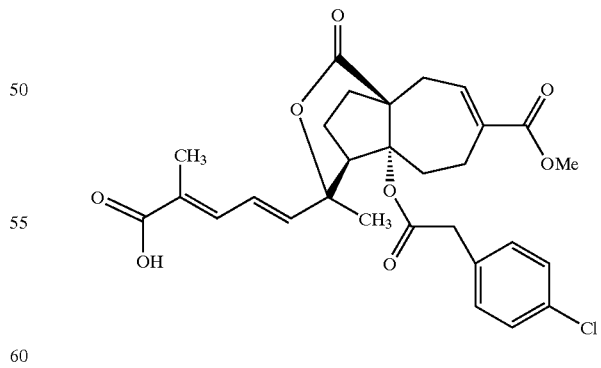

PEX-24Y 0.050 g (0.129 mmol), AgCN 0.172 g (1.28 mmol) and 0.5 ml ethyl ether were added to a flask. At room temperature, 3 mL p-chlorine-phenyl-acetyl chlorine was dropped to the mixture. After 24 h, the mixture was filtrated to remove AgCN and filtrate was then removed p-chlorine-phenyl-acetyl chlorine and ethyl ether under pressure. The residue was purified by silica gel column and eluted with petroleum:ethyl acetate:formic acid=3:1:0.1 to give PEX-24Y 0.030 g (43.0%).

$^1$HNMR (CDCl$_3$) δ (ppm): 1.56 (s, 3H), 1.94 (s, 3H), 3.64 (s, 2H), 3.72 (s, 3H), 5.87 (d, 1H, J=15.6Hz), 6.52 (dd, 1H, J=15.6, 11.2Hz), 7.21–7.36 (m, 6H). IR (KBr) (cm$^{-1}$): 3434.7, 1737.6, 1708.6, 1643.1, 1492.7, 1438.7, 810.0, 771.4.

EXAMPLE 6

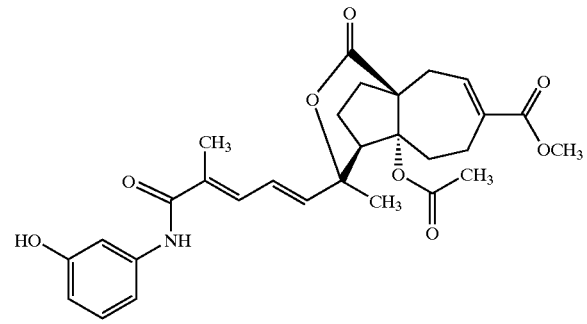

PEX-15Y

Step 1: 0.030 g (0.069 mmol) pseudolaric acid B and 1 mL ethyl ether were added and then 0.5 mL SOCl$_2$ was dropped at room temperature. After stirred for 1 h, the mixture was heated to 40–50° C. and kept at the temperature for 3 h. The mixture was then cooled to room temperature and the exceeding SOCl$_2$ was removed under pressure. 1 mL ethyl ether was added to form solution A.

Step 2: The flask containing 3 ml acetone, 1 mL water, 0.10 g (1.2 mmol) NaHCO$_3$ and 0.10 g (0.92 mmol) p-hydroxylanline was cooled to –2° C. Above solution A was slowly dropped and then the reaction was keep at about 0° C. After about 1 h, the mixture was adjusted to pH=6 (acetic acid) and removed acetone under pressure. Water phase was extracted with ethyl ether and the extract was purified by silica gel column (chloroform:methanol=10:1) to afford PEX-15Y 0.030 g (82.6%).

$^1$HNMR (DMCO) δ (ppm): 1.61 (s, 3H), 2.02 (s, 3H), 2.17 (s, 3H), 3.69 (s, 3H), 6.12 (d, 1H, J=15.2Hz), 6.52–6.58 (m, 2H), 6.99 (d, 1H, J=11.0Hz), 7.06–7.12 (m, 3H). IR (KBr) (cm$^{-1}$): 3390.3, 1739.5, 1716.4, 1648.9, 1602.6, 1500.0, 1444.4, 775.3, 690.4.

EXAMPLE 7

Preparation of the Pharmaceutical Composition

Formula

| Component | Amount |
|---|---|
| PEX-25Y | 200 mg |
| Ethanol | 2 ml |
| Methylcellose | 0.2 ml |
| Normal saline | 7.0 ml |
| Tween 80 | 0.8 ml |

Method of Preparation: 200 mg of PEX-25Y, 0.8 mg of Tween 80 and 2 ml ethanol were added into a morta and ground homogeneously. 5 minutes later, 7.0 ml of normal saline and 0.2 ml of methylcellose were added to form a solution containing 20 mg/ml PEX-25Y.

EXAMPLE 8

30 Kunming strain female mice weighing 18–22 g were used. Suspensions of well grown Sarcoma 180 cell were implanted subcutaneously into the right axilla region of the mice, about 4.5–5×10$^6$ cells/mouse. The animals were grouped randomly 24 hours after the implantation. Daily treatment with drugs or normal saline commenced 1 day after implantation of S-180 cells. Mice were administered by i.p. injection with vehicle or compounds once a day for consecutive 6 days. All the mice were euthanized after the last administration. The mice and the tumors were weighed. The average weights of tumors of each group were calculated and rate of inhibition of tumor growth in vivo was calculated using the following formula:

Growth inhibition (%) = $\left(1 - \dfrac{\text{Average tumor weigh of test group}}{\text{Average tumor weigh of control}}\right) \times 100\%$ Results:

| Group | Dosage | Number of mice | | Body weight (g) | | Tumor weight (g) | Inhibition % |
|---|---|---|---|---|---|---|---|
| | | Beginning | At last | Beginning | At last | | |
| PEX-25Y | 5 mg/kg | 10 | 10 | 20.4 | 21.1 | 0.30 ± 0.23 | 64.3 |
| PEX-25Y | 10 mg/kg | 10 | 9 | 20.4 | 19.7 | 0.26 ± 0.11 | 69.0 |
| PEX-25Y | 15 mg/kg | 10 | 10 | 20.5 | 21.2 | 0.28 ± 0.13 | 66.7 |
| Control | — | 20 | 17 | 20.7 | 21.5 | 0.84 ± 0.25 | — |

The above examples are only used to illustrate the preparation of compounds and pharmaceutical compositions of the invention and the pharmacological experiment results thereof. Those skilled in the art can make various modifications and alterations without departing from the spirit and scope of the invention. All these modifications and alterations will be covered by the claims.

What is claimed is:

1. Pseudolaric acid-B derivatives having general formula (I):

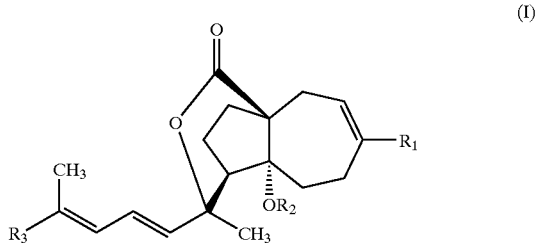

wherein
(a) $R_1$ is cyano, heterocyclyl, COXR' or CON(R")$_2$, wherein X is O or NH, R' is H, cycloalkyl, alkyl, heterocyclic alkyl or arylalkyl, each R" is independently alkyl, cycloalkyl or heterocyclicalkyl;
(b) $R_2$ is H, alkylacyl, arylalkylacyl, arylacyl or heterocyclylacyl; and
(c) $R_3$ is COXY, amino or halogen, wherein X is O or NH, Y is H, $NH_2$, hydroxy, alkyl, cycloalkyl, heterocyclicalkyl, hetroatom-substituted alkyl, tertiary amino-substituted ammonioalkyl, aryl, arylalkyl or polyhydroxyalkyl, Provided that pseudolaric acid A, pseudolaric acid B, pseudolaric acid C, pseudolaric acid $C_2$, deacetoxyl pseudolaric acid A, deacetoxyl pseudolaric acid $C_2$, methyl pseudolarate A, deacetoxyl methyl pseudolarate A, p-bromine phenacyl pseudolarate A, methyl pseudolarate B, p-bromine phenacyl pseudolarate B, methyl pseudolarate C, propyl pseudolate C, iso-propyl pseudolate C, 19-demethoxyl iso-propyl pseudolarate B, 19-demethoxyl iso-propyl pseudolarate C, 19-propyoxyl pseudolarate B, 19-propoxyl pseudolaric acid C, 19-butoxyl pseudolaric acid B, and 19-butoxyl pseudolaric acid C are excluded.

2. Pseudolaric acid-B derivatives according to claim 1 wherein $R_1$ is CONHR' or CON(R")$_2$, $R_2$ is H, an alkylacyl, an arylalkylacyl, an arylacyl, or a heterocyclic acyl, and $R_3$ is —COOH.

3. Pseudolaric acid-B derivatives according to claim 1 wherein $R_1$ is —COOR', $R_2$ is H, an alkylacyl, an arylalkylacyl, an arylacyl, or a heterocyclic acyl, and $R_3$ is —COOH.

4. Pseudolaric acid-B derivatives according to claim 1 wherein $R_1$ is —COOR', $R_2$ is H, an alkylacyl, an arylalkylacyl, an arylacyl, or a heterocyclic acyl, and $R_3$ is COXY.

5. A process for preparing the pseudolaric acid-B derivatives according to claim 1, comprising the steps of:
a. In case $R_1$ is CONHR or CONR'R", aminolyzing a compound of formula (I) wherein $R_1$ is COOR' in a water solution of an amine (said compound:said amine=1:1~1:300) in the presence of an acid catalyst at the conditions of temperature from −10° C. to 100° C. and pH 1–6;
b. In case $R_1$ is COOR', alcoholyzing a compound of formula (I) wherein $R_1$ is COOR' with an excess alcohol (said compound:said alcohol=1:1~1:500) in the presence of an alkali catalyst under anhydrous condition at a temperature from 0° C. to the reflux temperature of the solvent and pH 9–14;
c. In case $R_2$ is alkylacyl, aryl-substituted alkylacyl, arylacyl or heterocyclylacyl, acylating a compound of formula (I) wherein $R_2$ is H (said compound:acylating agent=1:5~1:500) at a temperature from 0° C. to 80° C.; or
d. In case $R_3$ is COXY, reacting a compound of formula (I) wherein $R_3$=COOH with an excess acyl halogenating agent to form an acyl halide, then reacting said acyl halide with an alcohol or an amine in the presence of an acid scavenger at a temperature between −20~30° C.

6. The process according to claim 5, wherein said acid catalyst is selected from a group consisting of HCl, $CH_3CO_2H$, $H_2SO_4$ and $H_3PO_4$.

7. The process according to claim 5, wherein said alkaline catalyst is selected from a group consisting of sodium amide, potassium amide, sodium alkoxide and potassium alkoxide, preferably, sodium alkoxide and potassium alkoxide.

8. The process according to claim 7, wherein said alkaline catalyst is selected from sodium alkoxide and potassium alkoxide.

9. The process according to claim 5, wherein said acylating agent is an acyl halide.

10. The process according to claim 5, wherein said halogenating agent is selected from a group consisting of $SOCl_2$, $POCl_3$, $PCl_5$, $S_2Cl_2$, $PBr_3$ and $PCl_3$.

11. The process according to claim 5, wherein said acid scavenger is selected from a group consisting of organic amine, $CaCO_3$, $K_2CO_3$, $Na_2CO_3$, $NaHCO_3$, KOH and NaOH.

12. A pharmaceutical composition for the treatment of tumors or inhibition of fungi, comprising a therapeutically effective amount of compound of claim 1 and a pharmaceutically acceptable carrier.

* * * * *

UNITED STATES PATENT AND TRADEMARK OFFICE
CERTIFICATE OF CORRECTION

PATENT NO. : 6,887,895 B2
DATED : May 3, 2005
INVENTOR(S) : Jianmin Yue et al.

It is certified that error appears in the above-identified patent and that said Letters Patent is hereby corrected as shown below:

Title page,
Item [75], should read:
-- Inventors   Jianmin YUE, Shanghai (CN);
               Shengping YANG, Shanghai (CN);
               Jian DING, Shanghai (CN);
               Dong XIAO, Shanghai (CN);
               Shengtao YUAN, Shanghai (CN);
               Yan WU, Shanghai (CN);
               Yunguang TONG, Shanghai (CN); and
               Lei DONG, Shanghai (CN). --.

Signed and Sealed this

Fourth Day of October, 2005

JON W. DUDAS
*Director of the United States Patent and Trademark Office*